United States Patent [19]

Kessler et al.

[11] 4,263,115

[45] Apr. 21, 1981

[54] ION-SELECTIVE ELECTRODE DEVICE FOR POLAROGRAPHIC MEASUREMENT OF OXYGEN

[75] Inventors: Manfred Kessler; Jens Höper, both of Dortmund, Fed. Rep. of Germany

[73] Assignee: Max Planck Gesellschaft zur Förderung der Wissenschaften, Göttingen, Fed. Rep. of Germany

[21] Appl. No.: 921,259

[22] Filed: Jul. 3, 1978

[51] Int. Cl.³ .......................................... G01N 27/30
[52] U.S. Cl. ............................................... 204/195 P
[58] Field of Search ............ 204/195 P, 195 M, 195 L

[56] References Cited

U.S. PATENT DOCUMENTS 3,857,777  12/1974  Guilbault et al. ............... 204/195 M
3,957,607   5/1976  Simon et al. .................... 204/195 M

OTHER PUBLICATIONS

The Condensed Chemical Dictionary, 7th Ed., Reinhold Book Corp., pp. V & 920.

*Primary Examiner*—Howard S. Williams
*Attorney, Agent, or Firm*—Michael J. Striker

[57] ABSTRACT

An ion-selective electrode device for measuring oxygen concentrations comprises a noble metal reduction electrode connected to a voltage source; a reference electrode connected to said reduction electrode; an ion-selective carrier or ligand membrane disposed in front of the reduction electrode and containing a cation-selective ligand and being permeable to hydrogen ion; a closure membrane to seal the device against the outside atmosphere, the said closure membrane being permeable to oxygen and impermeable to water, and an electrolyte containing the ligand cation of said ligand membrane, the said electrolyte being disposed between the said ligand membrane and said closure membrane.

12 Claims, 1 Drawing Figure

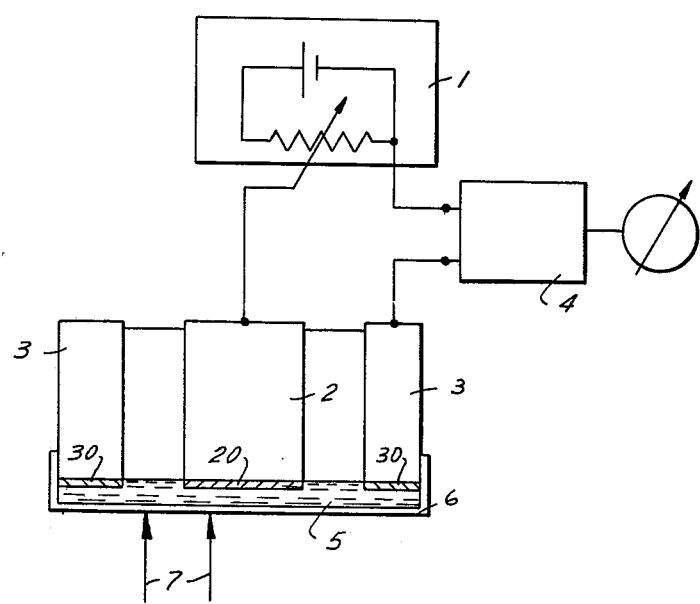

ION-SELECTIVE ELECTRODE DEVICE FOR POLAROGRAPHIC MEASUREMENT OF OXYGEN

BACKGROUND OF THE INVENTION

The invention relates to a device for the polarographic measurement of oxygen.

The prior art devices of this type have two important shortcomings.

On the one hand, even highly purified noble metals used in the electrodes do not prevent the transmission of foreign matters to the electrodes which thus exhibit drift phenomena which interfere with a long service time.

On the other hand, there occurs an oxygen consumption by the measurement itself which is so high that it interferes with the diffusion field in the most frequently measured organic tissues. As a consequence, the true oxygen concentration can be obtained either not at all or only after overlong times for the measurement.

It is therefore an object of the invention to avoid these shortcomings.

SUMMARY OF THE INVENTION

This is accomplished by a device comprising a source of potential voltage; a reduction electrode for the oxygen composed of a noble metal and connected to said voltage source; a reference electrode connected to said reduction electrode; a ligand membrane provided in front of the reduction electrode, the ligand membrane containing a cation-selective carrier and being permeable to hydrogen ions; a closure membrane to seal the electrodes against the outside space, the closure membrane being permeable to oxygen and impermeable to water, and an aqueous electrolyte containing the ligand cation of the ligand membrane, the said electrolyte being disposed between said ligand membrane and said closure membrane.

By virtue of this device the selective action of the ligand membrane causes only the reaction material to come in contact with the reduction electrode while no such contact takes place with the materials of which the electrolyte or the opposite electrode are composed. Chemical changes in the reduction electrode are thus avoided and the time of constant operation of the device is substantially extended. Furthermore, the particle flow of the oxygen is drastically reduced. An interference of the concentration field of the oxygen through the measurement activity is therefore extremely small.

The signal produced is measured by means of an amplifier which in order to preserve the above advantages should have an input value of about $10^{12}$ $\Omega$.

The device operates with particular success if the ligand is Na-selective. It has been found that in that case an easily indicated signal which is highly proportional to the actual oxygen concentration is produced.

The ligands or ion-sensitive molecule may be 3,6-dioxaoctanediacid-bis-diphenylamine, or preferably may consist of N,N,N,N-tetrabenzyl-3,6-dioxaoctane diamide or N,N'-dibenzyl-N,N'-diphenyl-1,2-phenylenedioxydiacetamide.

In a special embodiment of the invention the ion selective reference electrode is covered by a corresponding reference ligand membrane which contains an ion-sensitive molecule or ligand different from the cation ligand of the ligand membrane. This will protect the reference electrode from physical or chemical damage.

The electrolyte preferably consists of 0.1 M HCl and 0.01 M NaCl. NaCl and HCl are required for the function of the oxygen electrode 2 if the electrode consists of platinum covered with an Na+ membrane. On the other hand 0.01 M KCl should be used for the electrode if the reference electrode consists of platinum covered with a K+ membrane.

Preferably, the voltage provided is 200 mV. In this manner at the boundary layer of the platinum a $P_{O_2}$ dependent oxygen potential is generated.

The resistance of the electrode is:

$$R_{po2} + R_{mem} = \frac{U_{Po2} + U_{volt}}{I}$$

$R_{Po2}$ = resistance of polarization layer (Helmholtz layer)
$R_{membrane}$ = resistance of Na+ membrane
$U_{Po2}$ = oxygen potential
$U_{volt}$ = voltage of basic source The total resistance is in the range of $10^{10}$ Ohms and decreases by less than one order of magnitude with an increasing oxygen potential.

As already pointed out the membranes are preferably made of PVC impregnated with a solvent containing the ion-sensitive molecule. The membrane is for instance made by setting up a solution of PVC in dibenzyl ether. The solution is then mixed with about 0.6% by weight of the Na-ligand or 2.7% weight of the K-ligand (such as valinomycin) and subjected to drying. Thus, membranes of a thickness down to a few microns are obtained.

These membranes are then placed onto a body of PVC comprising the platinum electrodes and are welded together with the main body chemically by using again a small amount of solvent. The thus formed structure is then covered with a membrane of PVC or Teflon which does not contain a ligand. The space between the two membranes in the device is thereafter filled with an electrolyte.

It should be noted that the electrolyte does not contain the ligand itself, but only the ions.

With the device of the invention oxygen concentrations can be measured in a range of pressure from 1/100 mm mercury up to several psi. The measurement can be carried out amperometrically, that is with a measuring resistance of about $10^6$ $\Omega$ which will cause a stationary particle flow in the measuring system.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The single FIGURE of the drawing shows in a diagrammatic form the device of the invention.

DESCRIPTION OF PREFERRED EMBODIMENTS

A source of polarization voltage 1 of 200 mV is connected with the reduction electrode 2 which preferably consists of platinum. Another electrode, the reference electrode 3, is arranged in annular manner around the reduction electrode.

In front of the reduction electrode a PVC membrane (20) is arranged which contains an ion selective cation molecule or ligand and is permeable to hydrogen ions and oxygen.

In front of the other electrode, the reference electrode 3, a similar membrane, the reference ligand membrane 30, is provided which, however, contains an ion-sensitive molecule or ligand which is different from the ligand of the ligand membrane 20.

As has been noted above the device can be operated also without the reference ligand membrane.

The ion-sensitive molecule provided in the ligand membrane may consist of any of the products listed above and in the example was formed of 3,6-dioxaoctanediacid-bis-diphenylamine.

An electrolyte 5 is disposed so as to cover the entire device. The device is furthermore sealed against the exterior space by a closure membrane 6 which may be of polymerized tetrafluoroethylene synthetic plastic, commercially available under the trade name "Teflon". If no reference ligand membrane 30 is provided the electrolyte may consist only of 0.1 M HCl and 0.01 M NaCl. If a reference ligand membrane such as the membrane 30 is provided the electrolyte must additionally also contain the ion of the ligand used in the latter membrane, e.g. KCl.

The operation of the device is as follows: In the exterior space there is a specific concentration of the oxygen 7. The oxygen then will diffuse through the closure membrane 6 which may be made of Teflon and furthermore will penetrate together with the hydrogen ions from the electrolyte 5 into the ligand membrane 20. After reduction of the oxygen water is formed with the hydrogen ions according to the equation $$O_2 + 4e \rightarrow 2O^{--} + 4H^+ = 2H_2O$$

This reaction results in a change of potential of the electrode 2–20 in the chain of potential formed by the electrodes 2–20, 3–30, the electrolyte 5 and the voltage source 1. This change of potential is then indicated by means of the amplifier 4. As already noted the amplifier 4 has an input resistance of about $10^{12}$ Ω.

It will be understood that the electrolyte in case of the use of a reduction membrane and a reference membrane must contain the ions of both ligands. For instance, if the ions are Na+ and K+ in the case of an Na-ligand membrane used on the electrode 2 and in case of a K+ ligand membrane on the reference electrode 3 the electrolyte must contain both Na+ and K+ ions.

The polarization voltage is generated by a battery-driven, stabilized, and highly insulated power supply which is connected in series to the oxygen electrode. The slope of the calibration curve increases with higher polarization voltage. At a polarization voltage of $-200$ mV there was obtained a linear calibration curve with a slope of approximately 40 mV per decade of oxygen tension.

The sealing of the cathode with an ion-selective PVC membrane provides the following advantages:
1. The cathode is protected against deposition of metals and other reducible species in an almost ideal way.
2. The platinum interface is not in contact with an aqueous phase.
3. The ions which are supposed to be involved in the electrochemical reaction can be selected.

The oxygen sensor described is very suitable for tissue measurements because of its small convection sensitivity, its high sensitivity in the low $PO_2$ range and its relatively small drift.

The device can be used for $PO_2$ measurements in:
1. gases,
2. blood,
3. tissues (brain, heart, liver, kidney, skeletal muscle),
4. skin (noninvasive measurements of arterial $Po_2$).

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. An ion-selective electrode device for measuring oxygen concentrations comprising
   a source of potential voltage;
   a reduction electrode for the oxygen composed of a noble metal and connected to said voltage source;
   a reference electrode annularly disposed about said reduction electrode;
   a ligand membrane provided in front of the reduction electrode, the said ligand membrane containing a cation-selective carrier and being permeable to hydrogen ions;
   a closure membrane to seal the said electrodes against the outside space, the closure membrane being permeable to oxygen and impermeable to water, and an aqueous electrolyte containing the ligand cation of the said ligand membrane, the said electrolyte being disposed between said ligand membrane and said closure membrane.

2. The device of claim 1 in which said ligand membrane is a solvent-impregnated PVC containing said ion-selective ligand.

3. The device of claim 2 in which the ion-selective ligand of the ligand membrane is Na+ selective and the solvent is dibenzylether.

4. The device of claim 2 in which the said ion selective cation ligand is K+ selective and the solvent is (bis-(2-ethylhexyl) phthalate).

5. The device of claim 1 in which the cation selective ligand is a molecule selected from the group consisting of
   N,N,N,N-tetrabenzyl-3,6-dioxaoctane diamide, N,N'-dibenzyl-N,N'-diphenyl-1,2-phenylenedioxydiacetamide,
   3,6-dioxaoctanediacid-bis-diphenylamine, and valinomycin.

6. The device of claim 1 in which the electrolyte consists of 0.1 M HCl and 0.01 M NaCl if the ligand membrane is Na+ sensitive and contains 0.1 M HCl and 0.01 M KCl if the reference electrode membrane contains a K+ sensitive molecule.

7. The device of claim 1 which includes an amplifier for indicating the measurement produced by the device, the said amplifier having an input resistance of $10^{12}$ Ω.

8. The device of claim 1 wherein the reduction electrode is composed of platinum.

9. The device of claim 1 wherein the closure membrane is of polymerized tetrafluoroethylene.

10. The device of claim 1, which includes a reference membrane disposed in front of the reference electrode and containing a ligand different from the cation ligand of said ligand membrane, and wherein said electrolyte is in contact with said ligand membrane and said closure membrane and contains the ligand of the reference membrane in addition to the ligand of the ligand membrane.

11. The device of claim 10, wherein the ion of the ligand membrane is $Na^+$ and the ion of the reference membrane is $K^+$ or reverse and wherein the electrolyte contains both the $Na^+$ and $K^+$ ions.

12. The device of claim 10 wherein the reference electrode is arranged in ring-shape around said reduction electrode.